United States Patent [19]

Derungs

[11] Patent Number: 4,582,844

[45] Date of Patent: Apr. 15, 1986

[54] ANTITHROMBOTIC 4,5 DI-T-BUTYL-IMIDAZOLE DERIVATIVES

[75] Inventor: Romano Derungs, Riehen, Switzerland

[73] Assignee: Hoffmann-La Roche Inc., Nutley, N.J.

[21] Appl. No.: 774,393

[22] Filed: Sep. 10, 1985

Related U.S. Application Data

[63] Continuation of Ser. No. 493,886, May 12, 1983, abandoned, which is a continuation of Ser. No. 267,273, May 26, 1981, abandoned.

[30] Foreign Application Priority Data

Jun. 5, 1980 [CH] Switzerland .................. 4347/80

[51] Int. Cl.⁴ .................. A61K 31/415; C07D 233/64; C07D 405/10; C07D 409/04
[52] U.S. Cl. .................. 514/396; 514/397; 514/400; 548/323; 548/336; 548/346
[58] Field of Search .................. 548/336, 346; 514/397, 514/400, 396

[56] References Cited

U.S. PATENT DOCUMENTS 3,279,918 10/1966 Cassiers et al. .................. 548/346 X
3,473,901 10/1969 Deubenneville et al. .......... 548/347
3,652,581 3/1972 Spaenig et al. .................. 548/346 X

FOREIGN PATENT DOCUMENTS 775028 5/1972 Belgium .................. 548/346
2701372 1/1977 Fed. Rep. of Germany ...... 548/347
2733466 2/1979 Fed. Rep. of Germany .
99787 6/1969 German Democratic Rep. .................. 548/347

OTHER PUBLICATIONS

Chemical Abstracts, 75:123487v (1971) [Visser, G., et al., *Acta Crystallogr.*, Sect. B, 1971, 27 (Pt. 9), 1802–11].

Derwent Abstract of German OLS No. 2132079, 1/11/73.
Derwent Abstract of German OLS No. 2262187, 6/20/74.
Chemical Abstracts, vol. 56, Subject Index, p. 91N.
Ijpac Report on Nomenclature, *J. Am. Chem. Soc.*, 82, 5517 (1960).

*Primary Examiner*—Richard A. Schwartz
*Attorney, Agent, or Firm*—Jon S. Saxe; Bernard S. Leon; Matthew Boxer

[57] ABSTRACT

Imidazole derivatives of the formula

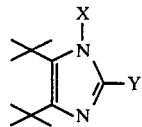

wherein X is hydrogen or $C_{1-4}$-n-alkyl and Y is thienyl, optionally substituted by methyl or fluorine, or a group of the formula

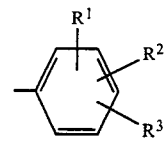

wherein $R^1$, $R^2$ and $R^3$ independently are hydrogen, methyl, fluorine, hydroxy or methoxy, or two of $R^1$, $R^2$ and $R^3$ on adjacent carbon atoms taken together are methylenedioxy or ethylenedioxy, or one of $R^1$, $R^2$ and $R^3$ is mono- or di-($C_{1-4}$-n-alkyl)-amino and the other two are hydrogen, and physiologically compatible or pharmaceutically acceptable acid addition salts thereof, are described. These compounds of formula I inhibit the aggregation of the blood platelets.

8 Claims, No Drawings

ANTITHROMBOTIC 4,5 DI-T-BUTYL-IMIDAZOLE DERIVATIVES

This is a continuation of application Ser. No. 493,886 filed May 12, 1983, now abandoned, which is a continuation of Ser. No. 267,273, filed May 26, 1981, now abandoned.

BRIEF SUMMARY OF THE INVENTION

Imidazole derivatives of the formula

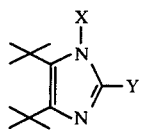

wherein X is hydrogen of $C_{1-4}$-n-alkyl and Y is thienyl, optionally substituted by methyl or fluorine, or a group of the formula

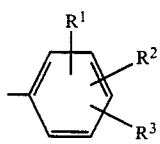

wherein $R^1$, $R^2$ and $R^3$ independently are hydrogen, methyl, fluorine, hydroxy or methoxy, or two of $R^1$, $R^2$ and $R^3$ on adjacent carbon atoms taken together are methylenedioxy or ethylenedioxy, or one of $R^1$, $R^2$ and $R^3$ is mono- or di-($C_{1-4}$-n-alkyl)-amino and the other two are hydrogen, and physiologically compatible or pharmaceutically acceptable acid addition salts thereof, are described. These compounds of formula I inhibit the aggregation of the blood platelets.

DETAILED DESCRIPTION OF THE INVENTION

The invention relates to imidazole derivatives of the formula

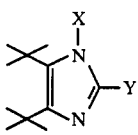

wherein X is hydrogen or $C_{1-4}$-n-alkyl, and Y is thienyl, optionally substituted by methyl or fluorine, or a group of the formula

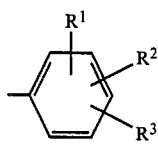

wherein $R^1$, $R^2$ and $R^3$ independently are hydrogen, methyl, fluorine, hydroxy or methoxy, or two of $R^1$, $R^2$ and $R^3$ on adjacent carbon atoms taken together are methylenedioxy or ethylenedioxy, or one of $R^1$, $R^2$ and $R^3$ is mono- or di($C_{1-4}$-n-alkyl)-amino and the other two are hydrogen, or a physiologically compatible or pharmaceutically acceptable acid addition salt thereof.

As used herein, the term $C_{1-4}$-n-alkyl denotes the straight-chain alkyl groups methyl, ethyl, propyl and butyl.

Preferred among the compounds of formula I are those wherein X is hydrogen and those wherein Y is a group of formula $Y^1$, especially p-fluorophenyl.

4,5-Di-t-butyl-2-(4-fluorophenyl)-imidazole is especially preferred.

The invention also relates to a process for the preparation of the aforementioned compounds as well as pharmaceutical preparations comprising the aforementioned compounds.

Examples of physiologically compatible or pharmaceutically acceptable acid addition salts are mineral acid salts such as hydrochlorides, hydrobromides, sulfates and phosphates, salts of organic sulfonic acids such as alkylsulfonates or arylsulfonates and carboxylic acid salts such as succinates or citrates.

The aforementioned compounds and salts can be prepared in accordance with the invention by treating a thiepinoimidazole of the formula

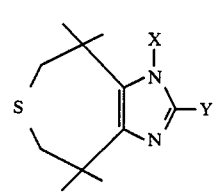

wherein X and Y are as previously described, or an acid addition salt thereof with a desulfurising catalyst and, if desired, converting a compound of formula I into an acid addition salt.

Examples of desulfurizing catalysts are metal catalysts such as nickel catalysts or palladium catalysts, preferably nickel catalysts, especially Raney-nickel. The desulfurization is conveniently carried out in a solvent, preferably a polar solvent such as dioxane or tetrahydrofuran at a temperature up to the reflux temperature.

The compounds of formula II wherein X is hydrogen can be prepared by reacting 3,3,6,6-tetramethyl-4,5-thiepanedione with an aldehyde Y—CH=O in the presence of ammonium ions, preferably in the presence of an ammonium salt such as ammonium acetate in a polar solvent such as dimethyl sulfoxide or dimethylformamide at a temperature up to the reflux temperature. The obtained compounds of formula II can be N-alkylated by reaction with an alkali metal hydride such as sodium hydride in a solvent such as dimethylformamide and reaction of the resulting compound with an alkyl halide such as methyl iodide.

The compounds of formula I and the physiologically compatible or pharmaceutically acceptable salts thereof can be used as medicaments. The compounds of formula I inhibit the aggregation of the blood platelets and can therefore be used for the prevention of thromboses.

The compounds of formula I can be used as medicaments, for example, in the form of pharmaceutical preparations which contain them or their salts in admixture with an organic or inorganic inert carrier material which is suitable for enteral or parenteral administration such as, for example, water, gelatin, gum arabic, lactose, starch, magnesium stearate, talc, vegetable oils, polyalkyleneglycols or the like. The pharmaceutical preparations can be made up in solid form, for example, as tablets, dragees, suppositories or capsules, or in liquid form, for example, as solutions, suspensions of emulsions. The pharmaceutical preparations may be sterilized and/or may contain adjuvants such as preserving, stabilizing, wetting or emulsifying agents, salts for varying the osmotic pressure or buffers. They can also contain still other therapeutically valuable substances. The oral administration of the compounds in accordance with the invention is preferred. For adult warm-blooded animals there comes into consideration an oral daily dosage in the range of from 0.5 to 30 mg/kg and a parenteral daily dosage in the range of from 0.05 to 10 mg/kg.

The aggregation-inhibiting activity was demonstrated according to the aggregometer method of BORN [Nature 194, 927 (1962)] and MICHAL and BORN [Nature 231, 220 (1971)]. The maximum aggregation velocity was taken as the test parameter and the effective concentration ($EC_{50}$) was ascertained from dosage-activity curves.

Human platelet-rich plasma was obtained by centrifugation from citrated venous blood. The experiments were carried out with suspensions of the test substances in 0.9% sodium chloride. 0.18 ml of citrate plasma was treated with a 10 μl suspension of the test compound and incubated at 37° C. for 10 minutes, whereupon the aggregation was initiated by adding 10 μl of a suspension of collagen fibrils.

The results are set forth in the following Table.

TABLE

| Collagen-induced blood platelet aggregation | |
|---|---|
| Compound | $EC_{50}$ (μM) |
| 4,5-Di-t-butyl-2-phenylimidazole | 0.6 |
| 4,5-Di-t-butyl-2-(4-fluorophenyl)-imidazole | 0.5 |
| 4,5-Di-t-butyl-2-(3,4-methylenedioxyphenyl)-imidazole | 0.55 |
| 4,5-Di-t-butyl-2-(5-methoxy-3,4-methylenedioxyphenyl)-imidazole | 14.4 |
| 4,5-Di-t-butyl-2-(3,4,5-trimethoxyphenyl)-imidazole | 0.72 |

The Examples which follow further illustrate the invention:

EXAMPLE 1

Preparation of 4,5-di-t-butyl-2-phenylimidazole 5 g of 2-Phenyl-4,5,7,8-tetrahydro-4,4,8,8-tetramethyl-1-H-thiepino[4,5-a]imidazole and 200 ml of dioxane are heated at reflux temperature for 20 hours, while stirring in the presence of a nickel catalyst (obtained by dehydrating 85 g of moist nickel catalyst with 300 ml of dioxane, whirling followed by sedimentation of the catalyst and removal of the solvent by suction.

The catalyst is then left to sediment in the reaction solution. The solution is filtered with suction. The catalyst is treated with 200 ml of dioxane and heated to boiling while stirring. After the catalyst has settled, the solution is again filtered by suction. This procedure is carried out once more.

The combined extracts are filtered and concentrated. After recrystallization from n-heptane, there are obtained 1.2 g of 4,5-di-t-butyl-2-phenylimidazole, m.p. 156°–158° C.

In order to prepare the hydrochloride, 604 mg of the base are dissolved in ether and the solution is neutralized by the dropwise addition of ethereal hydrochloric acid. The precipitate is removed by filtration and washed with ether and ethanol. There are obtained 680 mg of the hydrochloride, m.p 250°–255° C. (decomposition).

The thiepinoimidazole used as the starting material can be prepared as follows:

16 g of 3,3,6,6-tetramethyl-4,5-thiepanedione and 8 g of benzaldehyde are dissolved in 200 ml of dimethyl sulfoxide, 60 g of anhydrous ammonium acetate are added thereto with stirring and the mixture is heated at 90° C. After cooling, the reaction mixture is poured into ice-water while stirring, the solution is made alkaline with concentrated sodium hydroxide and extracted with ether. The organic phase is washed with ice-water and concentrated to dryness. The residue is covered with petroleum ether and rubbed with a glass rod. The precipitate which is removed by filtration is recrystallized from toluene and there is obtained 2-phenyl-4,5,7,8-tetrahydro-4,4,8,8-tetramethyl-1-H-thiepino[4,5-d]imidazole, m.p. 225°–227° C.

EXAMPLE 2

In a manner analogous to Example 1 there are obtained:

4,5-Di-t-butyl-2-(4-fluorophenyl)-imidazole, m.p. 185° C.; m.p. of the hydrochloride 240° C. (decomposition), 4,5-di-t-butyl-2-(4-methoxyphenyl)-imidazole, m.p. 145°–147° C.; m.p. of the hydrochloride 250° C. (decomposition), 4,5-di-t-butyl-2-(5-methoxy-3,4-methylenedioxyphenyl)-imidazole, m.p. 110°–113° C.; m.p. of the hydrochloride 210° C. (decomposition), 4,5-di-t-butyl-2-(3,4,5-trimethoxyphenyl)-imidazole, m.p. 140°–142° C.; m.p. of the hydrochloride 230° C. (decomposition), 4,5-di-t-butyl-2-phenyl-N-methylimidazole, m.p. 115°–117° C.; m.p. of the hydrochloride 205° C. (decomposition).

The thiepinoimidazole starting material used for the preparation of the last-named N-methylimidazole can be prepared as follows:

A suspension of 0.44 g of sodium hydride (55% in paraffin) in 10 ml of dimethylformamide is cooled to 0° C. under nitrogen or argon. Thereupon, there is added dropwise a solution of 2.86 g of 2-phenyl-4,5,7,8-tetrahydro-4,4,8,8-tetramethyl-1-H-thiepino[4,5-d]imidazole dissolved in 10 ml of dimethylformamide. The mixture is then left to react to completion at room temperature for 20 minutes. Then, 2.1 g of methyl iodide in 10 ml of dimethylformamide are added dropwise. The mixture is left to react to completion at room temperature for an additional 30 minutes. The reaction mixture is poured into ice-water while stirring, the precipitate is removed by filtration and washed in water. The filter residue is dissolved in ether and the solution is dried and concentrated. The suspension is treated with petroleum ether. After crystallization, the mixture is filtered and the product is recrystallized from n-heptane. The 2-phenyl-4,5,7,8-tetrahydro-1,4,4,8,8-pentamethyl-1-H-thiepino[4,5-d]imidazole melts at 158°–160° C. The melting point of the hydrochloride is 240° C. (decomposition).

EXAMPLE 3

Preparation of 4,5-di-t-butyl-2-(3,4-methylenedioxyphenyl)-imidazole 5.8 g of 2-(3,4-methylenedioxyphenyl)-4,5,7,8-tetrahydro-4,4,8,8-tetramethyl-1-H-thiepino[4,5-d]imidazole, 200 ml of tetrahydrofuran and a nickel catalyst (obtained by dehydrating 85 g of moist nickel catalyst with 300 ml of tetrahydrofuran, whirling followed by sedimentation of the catalyst and removal of the solvent by suction are heated at reflux temperature for 24 hours. The reaction solution is treated as described in Example 1, but using tetrahydrofuran in place of dioxane. After recrystallization from n-hexane, there are obtained 3.5 g of 4,5-di-t-butyl-2-(3,4-methylenedioxyphenyl)-imidazole, m.p. 175°–178° C.

In a manner analogous to Example 1, from 3.2 g of base, 3.5 g of hydrochloride are obtained, m.p. 200° C. (decomposition).

EXAMPLE 4

Tablets of the following composition are prepared in the usual manner:

| | |
|---|---|
| 4,5-Di-t-butyl-2-(4-fluorophenyl)-imidazole hydrochloride | 185.0 mg |
| Lactose | 15.0 mg |
| Maize starch | 37.9 mg |
| Water-soluble polyvinylpyrrolidone | 10.0 mg |
| Magnesium stearate | 2.5 mg |
| Total weight per tablet | 250.0 mg |

EXAMPLE 5

Interlocking gelatin capsules of the following composition are prepared in the usual manner:

| | |
|---|---|
| 4,5-Di-t-butyl-2-(4-fluorophenyl)-imidazole hydrochloride | 200.0 mg |
| Water-soluble polyvinylpyrrolidone | 2.0 mg |
| Maize starch | 43.0 mg |
| Talc | 4.5 mg |
| Magnesium Stearate | 0.5 mg |
| Total weight per capsule | 250.0 mg |

EXAMPLE 6

An injectable solution of the following composition is prepared in the usual manner:

4,5-Di-t-butyl-2-(4-fluorophenyl)-imidazole hydrochloride: 115.0 mg
Glycerinformal: 2.4 ml
Water for injection: 4.0 ml

I claim:

1. A compound of the formula

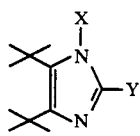

I wherein X is hydrogen or $C_{1-4}$-n-alkyl and Y is thienyl, optionally substituted by methyl or fluorine, or a group of the formula

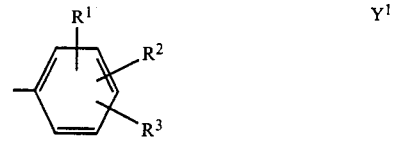

wherein $R^1$, $R^2$ and $R^3$ independently are hydrogen, methyl, fluorine, hydroxy or methoxy, or two of $R^1$, $R^2$ and $R^3$ on adjacent carbon atoms taken together are methylenedioxy or ethylenedioxy, or one of $R^1$, $R^2$ and $R^3$ is mono- or di-($C_{1-4}$-n-alkyl)-amino and the other two are hydrogen, or a pharmaceutically acceptable acid addition salt thereof.

2. A compound in accordance with claim 1, wherein X is hydrogen.

3. A compound in accordance with claim 1 or 2, wherein Y is the group of formula $Y^1$.

4. A compound in accordance with claim 1 or 2, wherein Y is p-fluorophenyl.

5. A compound in accordance with claim 1; 4,5-di-t-butyl-2-(4-fluorophenyl)-imidazole.

6. A compound in accordance with claim 1, selected from the group consisting of 4,5-di-t-butyl-2-phenylimidazole, 4,5-di-t-butyl-2-(4-methoxyphenyl)-imidazole, 4,5-di-t-butyl-2-(5-methoxy-3,4-methylenedioxyphenyl)-imidazole, 4,5-di-t-butyl-2-(3,4,5-trimethoxyphenyl)-imidazole, 4,5-di-t-butyl-2-phenyl-N-methylimidazole and 4,5-di-t-butyl-2-(3,4-methylenedioxyphenyl)-imidazole.

7. A blood platelet antiaggregation composition comprising an effective amount of a compound of the formula

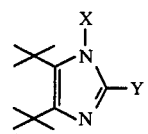

I wherein X is hydrogen or $C_{1-4}$-n-alkyl and Y is thienyl, optionally substituted by methyl or fluorine, or a group of the formula

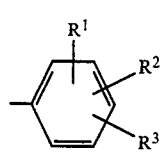

wherein $R^1$, $R^2$ and $R^3$ independently are hydrogen, methyl, fluorine, hydroxy or methoxy, or two of $R^1$, $R^2$ and $R^3$ on adjacent carbon atoms taken together are methylenedioxy or ethylenedioxy, or one of $R^1$, $R^2$ and $R^3$ is mono- or di-($C_{1-4}$-n-alkyl)-amino and the other two are hydrogen, or a pharmaceutically acceptable acid additon salt thereof, and an inert carrier.

8. A method of inhibiting blood platelet aggregation which comprises administering to a warm-blooded host an effective amount of a compound of the formula

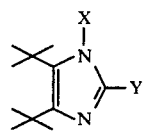

wherein X is hydrogen or $C_{1-4}$-n-alkyl and Y is thienyl, optionally substituted by methyl or fluorine, or a group of the formula

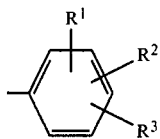

wherein $R^1$, $R^2$ and $R^3$ independently are hydrogen, methyl, fluorine, hydroxy or methoxy, or two of $R^1$, $R^2$ and $R^3$ on adjacent carbon atoms taken together are methylenedioxy or ethylenedioxy, or one of $R^1$, $R^2$ and $R^3$ is mono- or di-($C_{1-4}$-n-alkyl)-amino and the other two are hydrogen, or a pharmaceutically acceptable acid addition salt thereof.

* * * * *